(12) United States Patent
Hu et al.

(10) Patent No.: US 11,667,514 B2
(45) Date of Patent: Jun. 6, 2023

(54) QUANTITATIVE ESSENTIAL OIL DRIPPING DEVICE

(71) Applicant: Shenzhen Dituo Electronic Co., Ltd., Shenzhen (CN)

(72) Inventors: Yangmin Hu, Shenzhen (CN); Xiaolan Tang, Shenzhen (CN)

(73) Assignee: Shenzhen Dituo Electronic Co., Ltd., Shenzhen (CN)

( * ) Notice: Subject to any disclaimer, the term of this patent is extended or adjusted under 35 U.S.C. 154(b) by 560 days.

(21) Appl. No.: 16/708,456

(22) Filed: Dec. 10, 2019

(65) Prior Publication Data
US 2021/0039945 A1  Feb. 11, 2021

(30) Foreign Application Priority Data
Aug. 9, 2019 (CN) .......................... 201921287961.X (51) Int. Cl.
*B67D 7/22* (2010.01)
*B67D 7/36* (2010.01)
(Continued)

(52) U.S. Cl.
CPC ............... *B67D 7/222* (2013.01); *B05B 1/02* (2013.01); *B67D 7/0266* (2013.01); *B67D 7/36* (2013.01); *G05D 7/0664* (2013.01)

(58) Field of Classification Search
CPC .... B67D 7/222; B67D 7/0266; B67D 7/0272; G01N 2021/8564; A61M 5/1689; G07F 13/025; G07F 17/0092; G06Q 30/0607
See application file for complete search history.

(56) References Cited

U.S. PATENT DOCUMENTS

| | | | | |
|---|---|---|---|---|
| 4,676,404 A | * | 6/1987 | Yamazaki | ................ B67D 7/72 222/61 |
| 5,150,822 A | * | 9/1992 | Eitner, Jr. | ................ B05B 7/32 222/630 |

(Continued)

*Primary Examiner* — Andrew D StClair
(74) *Attorney, Agent, or Firm* — Chiesa, Shahinian & Giantomasi PC (57) ABSTRACT

A quantitative essential oil dripping device which includes: N sealed essential oil containers for containing essential oil, wherein N is a positive integer greater than or equal to 1; N gas inlet tubes and N oil outlet tubes, which are all inserted into the N essential oil containers respectively, wherein in each of the essential oil containers, a gas outlet of the gas inlet tube is located above an inlet of the oil outlet tube; a gas pump arranged at gas inlets of the N gas inlet tubes; a throttle valve communicating the gas pump with the essential oil container; and a drip number detection module configured to detect the drip number of the essential oil dripped from an oil outlet of the oil outlet tube. During use, the gas pump is started, pressure is applied to the essential oil container through the gas pump, and the essential oil is driven to be dripped from the oil outlet tube under the combined action of the gas pump and the throttle valve, thereby achieving the dripping of the essential oil. The drip number of the essential oil dripped from the oil outlet of the oil outlet tube is detected through the drip number detection module, and the amount of the dripped essential oil is measured by recording the drip number, thereby accurately controlling the dripping of the essential oil. After the dripping of the essential oil is completed, the gas pump is stopped.

13 Claims, 4 Drawing Sheets

(51) Int. Cl.
*B05B 1/02* (2006.01)
*G05D 7/06* (2006.01)
*B67D 7/02* (2010.01)

(56) References Cited

U.S. PATENT DOCUMENTS

| | | | |
|---|---|---|---|
| 5,551,309 A * | 9/1996 | Goossens | G05D 9/12 73/863 |
| 7,414,255 B1 * | 8/2008 | Amend | G01N 35/1016 250/573 |
| 2012/0014405 A1 * | 1/2012 | Anderson | G01N 33/2805 374/43 |
| 2016/0193615 A1 * | 7/2016 | Schmid | B05B 12/087 222/1 |
| 2019/0062144 A1 * | 2/2019 | Greenbaum | G07F 17/0092 |
| 2020/0077767 A1 * | 3/2020 | Artal Lahoz | A61L 9/01 |

\* cited by examiner

QUANTITATIVE ESSENTIAL OIL DRIPPING DEVICE

TECHNICAL FIELD

The present invention relates to a dripping device, and more particularly, to a quantitative essential oil dripping device.

BACKGROUND

Essential oil aromatherapy is a lifestyle that is gradually accepted by the world at present, and this lifestyle is becoming popular in European and American countries.

The aromatherapy is divided into single aromatherapy and compound aromatherapy depending on whether one or more than one essential oils are used. However, scientific aromatherapy, like dispensing medicine, is required to be quantitative, especially for the compound aromatherapy, for which a variety of essential oils must be mixed according to certain proportion to obtain a proper smell and effect. However, traditional quantitative oil blending is manually performed in general. That is, a container containing essential oil is inclined manually to drip the essential oil from a small hole, and then the drip number of the essential oil dripped is observed and counted so as to achieve the purpose of quantification. During the operation, an operator needs to memorize the formula and accurately control the amount of the essential oil dripped. As a result, only a professional operator may operate, and ordinary people may have operation difficulty. Thus, this operation method is not suitable for promotion. Therefore, there is an urgent need for an essential oil dripping device capable of quantitatively dripping essential oil.

SUMMARY

In order to facilitating achievement of accurate quantitative oil distribution, according to one aspect of the present invention, a quantitative essential oil dripping device is provided.

The quantitative essential oil dripping device includes N sealed essential oil containers configured to contain essential oil, wherein N is a positive integer greater than or equal to 1; N gas inlet tubes, of which gas outlets are inserted into the N essential oil containers respectively; N oil outlet tubes, of which inlets are inserted into the N essential oil containers respectively, wherein in each of the essential oil containers, the gas outlet of the gas inlet tube is located above the inlet of the oil outlet tube; a gas pump arranged at gas inlets of N gas inlet tubes and configured to fill the gas inlet tubes with gas; a throttle valve communicating the gas pump with the essential oil container; and a drip number detection module configured to detect the drip number of the essential oil dripped from an oil outlet of the oil outlet tube. Thus, when the quantitative essential oil dripping device is used, firstly, it needs to ensure that a liquid level in the essential oil container is located between the gas outlet of the gas inlet tube and the inlet of the oil outlet tube in the essential oil container. Subsequently, the gas pump is controlled to be started, and the gas pump may fill a accommodating chamber, which contains the essential oil, of the essential oil container with gas through the gas inlet tube. Since the essential oil container is sealed, the gas pump applies, through the gas inlet tube, pressure to the liquid level of the essential oil contained in the essential oil container. The gas flow in the gas inlet tube may also be adjusted through the throttle valve to prevent that too large gas flow of the gas pump causes a great impact on the essential oil in an essential oil bottle, resulting in linear outflow of the essential oil at a tail end of the oil outlet tube; and the essential oil is driven to be dripped from the oil outlet tube, thereby achieving the dripping of the essential oil. The drip number of the essential oil dripped from the oil outlet of the oil outlet tube is detected through the drip number detection module, so that accurate control on the dripping of the essential oil is achieved. After the dripping of the essential oil is completed, the gas pump is stopped.

In some embodiments, the quantitative essential oil-dripping device further includes N passage-selection electromagnetic valves arranged on the N gas inlet tubes respectively and configured to control the opening or closing of the gas inlet tubes, so that the essential oil container is communicated with or disconnected from the gas pump; and a main tube communicated with the gas inlets of all the N gas inlet tubes. The gas pump is communicated with the gas inlets of the N gas inlet tubes through the main tube. The throttle value is arranged on the gas inlet tube or the main tube between the selection electromagnetic valve and the gas pump. Thus, when the gas pump is started, it only needs to start the passage-selection electromagnetic valve communicated with the essential oil container from which the essential oil needs to be dripped and close the passage-selection electromagnetic valve communicated with the essential oil container from which no essential oil should be dripped, so that the gas flow in the gas inlet tube or the main tube may be adjusted through the throttle valve to prevent that too large gas flow of the gas pump causes a great impact on the essential oil in the essential oil container, resulting in linear outflow of the essential oil at the tail end of the oil outlet tube and thus inaccurate measurement of the essential oil dripped. Therefore, the accurate control on the drip number of the essential oil in different proportion is achieved.

In some embodiments, the quantitative essential oil-dripping device further includes a pressure-relief electromagnetic valve arranged on the main tube and configured to communicate the main tube with the outside or disconnect the main tube from the outside. Thus, after the dripping of the essential oil is completed and the gas pump is stopped, the main tube may be communicated with the outside by starting the pressure-relief electromagnetic valve, so that high-pressure gas in the essential oil container and the gas inlet tube is discharged from a second end of the main tube. Thus, the gas pressure in the essential oil bottle is balanced with the gas pressure outside and the essential oil remaining in the oil outlet tube flows back to the essential oil bottle, thereby reducing the corrosion of the essential oil to the oil outlet tube.

In some embodiments, connection portions of the N gas inlet tubes and the main tube are all located between the gas pump and the pressure-relief electromagnetic valve. Thus, the following case can be avoided: when the gas pump is started, as the pressure-relief electromagnetic valve is located on the main tube of the N gas inlet tubes, the amounts of gas flowing into the N gas inlet tubes are different.

In some embodiments, the quantitative essential oil dripping device further includes a buffer gas-storage chamber arranged at an end, away from the gas pump, of the main tube and communicated with the main tube. By arranging the buffer gas-storage chamber, a buffer effect on the gas flow in the main tube is achieved and the gas pressure fluctuation in the main tube is buffered, which facilitates stable dripping of the essential oil from the oil outlet tube.

In some embodiments, the drip number detection module includes a discharging constraint cover with N drip hole passages for insertion of and communication with the N oil outlet tubes; M groups of infrared ray pair tubes which are arranged on the discharging constraint cover, correspond to drip outlets of the N drip hole passages in position and are configured to detect essential oil drips, wherein M is a positive integer greater than or equal to 1; and a circuit board electrically connected with the M groups of infrared ray pair tubes and configured to perform counting. When it needs to detect the number of oil drips dripped from the oil outlet tube, firstly, the N oil outlet tubes are inserted into corresponding drip hole passages respectively, so that the oil outlet tubes are communicated with the drip hole passages respectively. When the essential oil is not dripped from the drip outlet of the drip hole passage, infrared rays between the infrared ray pair tube are not shielded or refracted. At this time, the infrared ray pair tube generates a first electrical signal. When the essential oil is dripped from the drip outlet of the drip hole passage, the infrared rays between the infrared ray pair tube is shielded or refracted. At this time, the infrared ray pair tube generates a second electrical signal. The circuit board receives the first electrical signal and the second electrical signal above and converts the same to pulse signals. A user may process the pulse signals and perform counting.

In some embodiments, the circuit board includes M groups of signal processing circuits which are electrically connected with the M groups of infrared ray pair tubes and configured to convert an electrical signal generated by electrical connection of the M groups of infrared ray pair tubes to a pulse signal; and a microprocessor electrically connected with the M groups of signal processing circuits and configured to perform counting according to the pulse signal. Thus, the pulse signals may be counted by the microprocessor and thus the quantitative essential oil dripping device has the function of accurately counting the essential oil drips.

In some embodiments, the M groups of infrared ray pair tubes include M infrared ray-emitting tubes and M infrared ray-receiving tubes which are all arranged on the circuit board and in one-to-one correspondence. The M infrared ray-emitting tubes are arranged at one side of the drip outlets of the N drip hole passages; the M infrared ray-receiving tubes are arranged at an opposite side of drip outlets of the N drip hole passages; and the M infrared ray-emitting tubes and the M infrared ray-receiving tubes face each other. Thus, the infrared ray-emitting tube emits infrared rays to the infrared ray-receiving tube. When no essential oil is dripped from the drip outlet of the drip hole passage, the infrared rays between the infrared ray-emitting tube and the infrared ray-receiving tube are not shielded or refracted. At this time, the infrared ray-receiving tube generates the first electrical signal. When essential oil are dripped from the drip outlet of the drip hole passage, the infrared rays between the infrared ray-emitting tube and the infrared ray-receiving tube are shielded or refracted. At this time, the infrared ray-receiving to tube generates the second electrical signal.

In some embodiments, the drip number detection module further includes a transparent inner cover configured to contain the M infrared ray-emitting tubes, the M infrared ray-receiving tubes and the circuit board so as to separate the M infrared ray-emitting tubes, the M infrared ray-receiving tubes and the circuit board from the drip outlets of the N drip hole passages. The inner cover is provided with a first transparent accommodating chamber located at one side of the drip outlets of the N drip hole passages and configured to contain the M infrared ray-emitting tubes, and a second transparent accommodating chamber located at the opposite side of the drip outlets of the N drip hole passages and configured to contain the M infrared ray-receiving tubes. The M infrared ray-emitting tubes and the M infrared ray-receiving tubes are arranged on the discharging constraint cover through the inner cover, so as to avoid failure of the M infrared ray-emitting tubes, the M infrared ray-receiving tubes and the circuit board or inaccuracy of detection data as the essential oil is dripped on the M infrared ray-emitting tubes, the M infrared ray-receiving tubes and the circuit board.

In some embodiments, N is a positive integer greater than or equal to 2, and M=1. The N drip hole passages include N horizontal hole passages, and N vertical hole passages correspondingly communicated with the N horizontal hole passages. A first end of each of the N horizontal hole passages extends to an end surface of a first end of the discharging constraint cover, and the N horizontal hole passages have the same length. One group of infrared ray pair tubes is arranged at two sides directly below the N vertical hole passages so as to detect the essential oil drips dripped from the N vertical hole passages. Therefore, the essential oil drips dripped from the plurality of drip hole passages are detected through one group of infrared ray pair tubes. During detection, the dripping of different drip hole passages may be controlled according to time periods. For example, within a first time period, a first oil outlet tube is controlled to discharge the essential oil and the essential oil is dripped from a first drip hole passage. At this time, the infrared ray pair tube counts the essential oil drips dripped from the first drip hole passage. After the completion of counting, the essential oil in the first oil outlet tube is controlled to stop entering the first drip hole passage. Within a second time period, a second oil outlet tube is controlled to discharge the essential oil and the essential oil is dripped from a second drip hole passage. At this time, the infrared ray pair tube counts the essential oil drips dripped from the second drip hole passage. After the completion of counting, the essential oil in the second oil outlet tube is controlled to stop entering the second drip hole passage. By such analogy, finally, the drip numbers for the plurality of drip hole passages are detected by one group of infrared ray pair tubes at different time periods.

In some embodiments, each two horizontal hole passages in the N horizontal hole passages are parallel to each other, and each two vertical hole passages in the N vertical hole passages are parallel to each other. Thus, the quantitative essential oil dripping device has a compact structure.

In some embodiments, M=N and both M and N are positive integers greater than or equal to 2. The N drip hole passages include N horizontal hole passages, and N vertical hole passages correspondingly communicated with the N horizontal hole passages. A first end of each of the N horizontal hole passages extends to an end surface of a first end of the discharging constraint cover, and the N horizontal hole passages have different lengths. Each of the M groups of infrared ray pair tubes corresponds to one vertical hole passage; each of the M groups of infrared ray pair tubes is correspondingly arranged at two sides directly below the each of M vertical hole passages; and each of the M groups of infrared ray pair tubes is configured to detect the essential oil drips dripped from one vertical hole passage. Therefore, the drip numbers of the essential oil dripped from the plurality of drip hole passages may be detected simultaneously through the plurality of groups of infrared ray pair tubes. Each drip hole passage corresponds to one group of infrared ray pair tubes, and when the drip number is detected, each group of infrared ray pair tubes detects the drip number of the essential oil dripped from the corresponding drip hole passage. The essential oil may be simultaneously dripped from the plurality of drip hole passages and the plurality of groups of drips may be counted simultaneously, so that the dripping efficiency is improved.

In some embodiments, each two horizontal hole passages in the N horizontal hole passages are parallel to each other. Thus, the quantitative essential oil dripping device has a compact structure.

In some embodiments, M=1 and N=1; the N drip hole passage is one drip hole passage; the M group of infrared ray pair tubes is one group of infrared ray pair tubes; and the one group of infrared ray pair tubes is arranged at two sides of the drip outlet of the one drip hole passage. Therefore, the essential oil drips dripped from the drip outlet of one drip hole passage is counted through the one group of infrared ray pair tubes.

DETAILED DESCRIPTION

The present invention is further illustrated in detail below with reference to the accompanying drawings.

Figure 1:
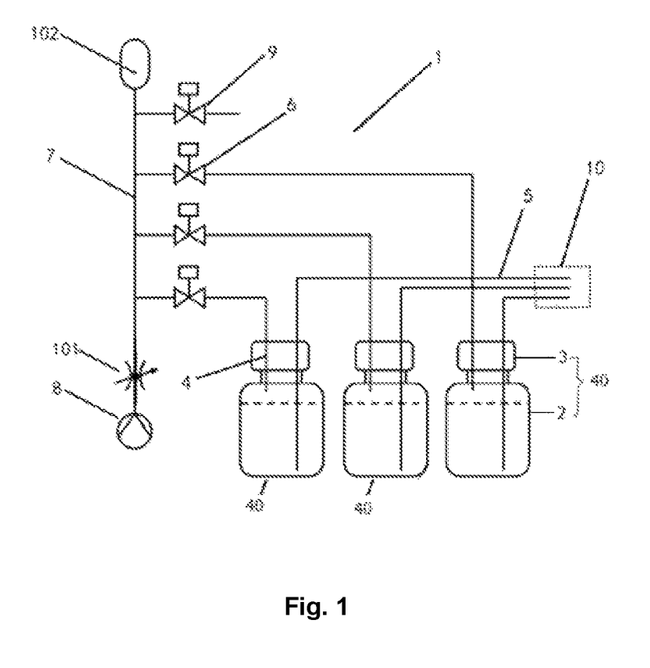
FIG. 1 is a structural diagram of a quantitative essential oil dripping device in the present invention.

FIG. 1 schematically shows a quantitative essential oil dripping device according one embodiment of the present invention.

As shown in FIG. 1, in the embodiment of the quantitative essential oil dripping device of the present invention, the dripping device 1 includes N sealed essential oil containers 40, N gas inlet tubes 4, N oil outlet tubes 5, a gas pump 8, a throttle valve 101 and a drip number detection module, wherein N is a positive integer greater than or equal to 1. The essential oil container 40 is configured to contain essential oil, a gas outlet of each gas inlet tube 4 is individually inserted into one essential oil container 40, an inlet of each oil outlet tube 5 is individually inserted into one essential oil container 40. In each of the essential oil containers 40, the gas outlet of the gas inlet gas 4 is higher than the inlet of the oil outlet tube 5. The gas pump 8 is communicated with gas inlets of all the gas inlet tubes 4, so that the gas pump 8 may fill the gas inlet tubes 4 with gas. The throttle vale 101 communicates the gas pump 8 with the essential oil container 40. The drip number detection module 10 detects the drip number of the essential oil dripped from an oil outlet of the oil outlet tube 5.

Thus, when the quantitative essential oil dripping device is used, firstly, it needs to ensure that a liquid level in the essential oil container 40 is located between the gas outlet of the gas inlet tube 4 and the inlet of the oil outlet tube 5 in the essential oil container 40. Subsequently, the gas pump 8 is controlled to be started, and the gas pump 8 may fill an accommodating chamber, which contains the essential oil, of the essential oil container 40 with gas through the gas inlet tube 4. Since the essential oil container 40 is sealed, the gas pump 8 applies, through the gas inlet tube 4, pressure to the liquid level of the essential oil contained in the essential oil container 40. The gas flow in the gas inlet tube 4 may also be adjusted through the throttle valve 101 to prevent that too large gas flow of the gas pump 8 causes a great impact on the essential oil in an essential oil bottle, resulting in linear outflow of the essential oil at a tail end of the oil outlet tube 5; and the essential oil is driven to be dripped from the oil outlet tube 5, thereby achieving the dripping of the essential oil. The drip number of the essential oil dripped from the oil outlet of the oil outlet tube 5 is detected through the drip number detection module 10, so that accurate control on the dripping of the essential oil is achieved. After the dripping of the essential oil is completed, the gas pump 8 is stopped.

Specifically, the drip number detection module 10 may be placed or arranged on the essential oil container 40, the gas inlet tube 4, the oil outlet tube 5, the gas pump 8 or the throttle valve 101. When the drip number detection module 10 is arranged on the essential oil container 40, for facilitating the replacement of the essential oil container 40, the drip number detection module 10 is detachably connected with the essential oil container 40. When the drip number detection module 10 is arranged on the gas inlet tube 4, the oil outlet tube 5, the gas pump 8 or the throttle valve 101, the drip number detection module 10 may be detachably or non-detachably connected with the gas inlet tube 4, the oil outlet tube 5, the gas pump 8 or the throttle valve 101, so that the drip number detection module 10 detects the drip number of the essential oil dripped from the oil outlet of the oil outlet tube 5. Moreover, the quantitative essential oil dripping device has a compact structure and is convenient to assemble. Preferably, as shown in FIG. 1, the drip number detection module 10 is arranged on the oil outlet tube 5 so as to detect the drip number of the essential oil dripped from the oil outlet of the oil outlet tube 5.

Specifically, a first specific implementation mode of the throttle valve 101 is that the throttle valve 101 is a valve capable of adjusting a flow rate in the prior art.

A second specific implementation mode of the throttle valve 101 is that the throttle valve 101 is arranged as a small hole that communicates two ends of the gas inlet tube 4, and the hole diameter of the small hole is arranged such that the essential oil in the essential oil container 40 is dripped from the oil outlet of the oil outlet tube 5 under the action of pressure of the gas introduced into the essential oil container 40 through the small hole by the gas pump 8.

Specifically, the gas pump 8 may be an electric gas pump, and the model and specification of the electric gas pump may be determined according to use requirements. For example, when a small amount of gas is required to be provided by the electric gas pump, a micro electric gas pump may be selected. More specifically, the gas pump 8 may be a gas pump with the model of YYPM20-3B1.

In a first arrangement mode of the gas pump 8, N gas pumps 8 may be arranged, and each gas pump 8 is individually communicated with the gas inlet of one gas inlet tube 4, so that the dripping of the essential oil in the essential oil container 40 communicated with the corresponding gas pump is individually controlled by each gas pump 8 and thus compound essential oils in different proportions may be prepared.

In a second arrangement mode of the gas pump 8, only one gas pump 8 may be arranged to reduce energy consumption. The gas pump 8 is communicated with all of the gas inlet tubes 4. Specifically, one gas pump 8 may be communicated with all the gas inlet tubes 4 through one main tube 7. More specifically, a gas inlet of the main tube 7 is communicated with the gas pump 8, at least N gas outlets are integrally formed or machined in the main tube 7, and each of the gas outlets is communicated with one gas inlet tube 4. At this time, the gas inlet tube 4 may be detachably connected with the gas pump 8 and/or the essential oil container 40, and the oil outlet tube 5 may also be detachably connected with the essential oil container 40 and the drip number detection module 10. When the essential oil in certain specific essential oil container 40 is not required to be dripped out, it only needs to detach the gas inlet tube 4 or the oil outlet tube 5 communicated with this essential oil container 40. The gas inlet tube 4 is, for example, detached from the gas pump 8 or the essential oil container 40, and the oil outlet tube 5 is, for example, detached from the essential oil container 40 or the drip number detection module 10, that is, a passage that communicates the essential oil container 40 with the gas pump 8 or a passage that communicates the essential oil container 40 with the drip number detection module 10 is blocked.

A third arrangement mode of the gas pump 8 is different from the above two arrangement modes in that a connection mode of the gas inlet tube 4 with the gas pump 8 and the essential oil container 40 is not limited; a connection mode of the oil outlet tube 5 with the essential oil container 40 and the drip number detection module 10 is not limited; and all that is needed is to arrange a passage-selection electromagnetic valve 6, which is capable of communicating or disconnecting two ends of the gas inlet tube 4, on the gas inlet tube 4, and to arrange the throttle valve 101 on the gas inlet tube 4 or the main tube 7 between the selection electromagnetic valve 6 and the gas pump, so that the two ends of the gas inlet tube 4 are communicated or the main tube 7 is communicated with the gas inlet tube 4 through the throttle valve 101. Thus, when the gas pump 8 is started, there is no need to detach the gas inlet tube 4 or the oil outlet tube 5, and all that is needed is to start the passage-selection electromagnetic valve 6 communicated with the essential oil container 40 from which the essential oil is dripped, and to close the passage-selection electromagnetic valve 6 communicated with the essential oil container 40 from which the essential oil should not be dripped. Consequently, accurate control on the drip number of the essential oil in different proportions may be achieved, thereby reducing energy consumption and achieving high convenience in operation.

Specifically, with continued reference to FIG. 1, the sealed essential oil container 40 may be implemented as including an essential oil bottle 2 with an 1*o* accommodating chamber capable of containing the essential oil, and a bottle cap 3. The accommodating chamber of the essential oil bottle 2 is communicated with the outside through an opening, and the bottle cap 3 hermetically covers the opening of the essential oil bottle 2, so that the accommodating chamber of the essential oil bottle 2 is separated from the outside. More specifically, an opening adapted to the gas inlet tube 4 and the oil outlet tube 5 is integrally formed or machined in the bottle cap 3, so that when the gas inlet tube 4 and the oil outlet tube 5 are adapted onto the bottle cap 3, the bottle cap 3 may be communicated with the outside through only the gas inlet of the gas inlet tube 4 and the oil outlet of the oil outlet tube 5. That is, a connection mode of the bottle cap 3 with the essential oil bottle 2, and a connection mode of the gas inlet tube 4 and the oil outlet tube 5 with the bottle cap 3 are all common sealed connection modes.

Further, as shown in FIG. 1, the quantitative essential oil dripping device further includes a pressure-relief electromagnetic valve 9. The pressure-relief electromagnetic valve 9 is arranged on the main tube 7 and is arranged to communicate the main tube 7 with the outside or disconnect the main tube 7 from the outside. Specifically, an opening for mounting of the pressure-relief electromagnetic valve 9 is integrally formed or machined in the main tube 7. Preferably, the gas pump 8 is connected with one end of main tube 7 and the pressure-relief electromagnetic valve 9 is connected with the opposite end of main tube 7. The gas inlet tube 4 is connected between the two ends, connected with the gas pump 8 and the pressure-relief electromagnetic valve 9 respectively, of the main tube 7. Specifically, the selection electromagnetic valve 6 and the pressure-relief electromagnetic valve 9 may be the same electromagnetic valve, such as the electromagnetic valve with the model of S0520AV-D.

Still further, with continued reference to FIG. 1, the quantitative essential oil dripping device further includes a buffer gas-storage chamber 102 arranged at an end, away from the gas pump 8, of the main tube 7 and communicated with the main tube 7. In other embodiments, it is also possible to achieve the buffer effect on the gas flow by lengthening the main tube 7 or increasing the inner diameter of the main tube 7.

Figure 2:
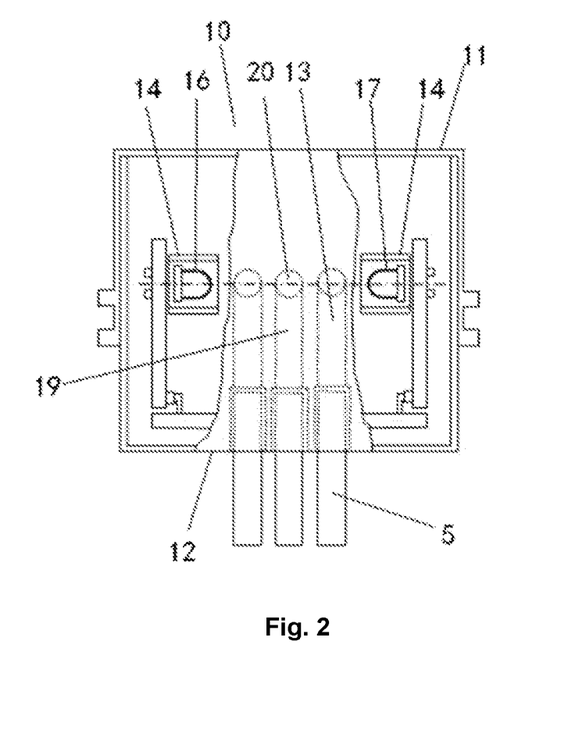
FIG. 2 is a structural diagram, viewed from above, of a first embodiment of a drip number detection module in the present invention.
Figure 4:
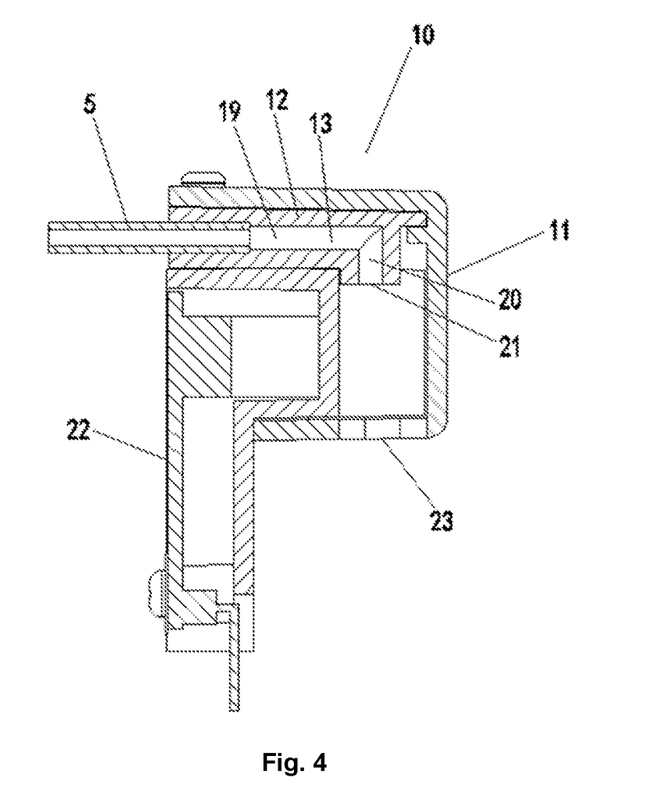
FIG. 4 is a sectional structural diagram of a drip number detection module in the present invention.

Specifically, a first implementation mode of the drip number detection module 10 is shown in FIG. 2 and FIG. 4. The drip number detection module 10 includes a discharging constraint cover 12, an infrared ray pair tube 14 and a circuit board 22 configured to perform counting. N drip hole passages 13 are integrally formed or machined in the discharging constraint cover 12. Each oil outlet tube 5 is individually inserted into one drip hole passage 13. There are M groups of infrared ray pair tubes 14, and M is a positive integer greater than or equal to 1. In addition, the M groups of infrared ray pair tubes 14 correspond to drip outlets 21 of the N drip hole passages 13 in position and are configured to detect the drip number of the essential oil dripped from the drip outlets 21 of the drip hole passages 13. The circuit board 22 is electrically connected with the M groups of infrared ray pair tubes 14. Specifically, the M groups of infrared ray pair tubes 14 may also be connected onto the discharging constraint cover 12 through the circuit board 22 or the circuit board 22 may be connected onto the discharging constraint cover 12 through the M groups of infrared ray pair tubes 14.

Figure 3:
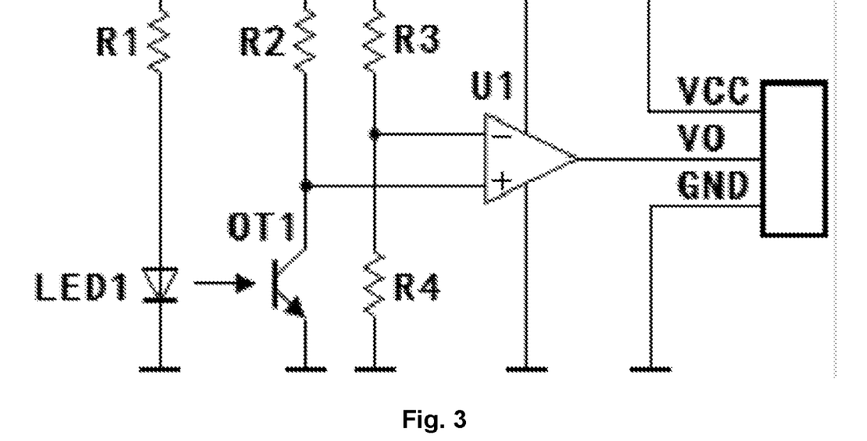
FIG. 3 is a circuit diagram of a signal processing circuit in a drip number detection module in the present invention.

The circuit board 22 includes M groups of signal processing circuits which are electrically connected with the M groups of infrared ray pair tubes 14 and configured to convert an electrical signal generated by the M groups of infrared ray pair tubes 14 to a pulse signal for counting; and a microprocessor electrically connected with the M groups of signal processing circuits and configured to perform counting according to the pulse signal. Specifically, a circuit diagram of the signal processing circuit is shown in FIG. 3. Each group of signal processing circuits corresponds to one group of infrared ray pair tubes 14 and converts the electrical signal generated by each group of infrared ray pair tubes 14 to the pulse signal. Further, the drip number detection module 10 may further include a display electrically connected with the microprocessor and configured to display counting information. A user may calculate the amount of the essential oil according to the drip number displayed on the display, and then control the opening or closing of each of the N passage-selection electromagnetic valves 6 according to the amount of essential oil. Specifically, the microprocessor may be a microprocessor with the model of NUC029.

Specifically, as shown in FIG. 2, the M groups of infrared ray pair tubes 14 include M infrared ray-emitting tubes 16 and M infrared ray-receiving tubes 17 which are in one-to-one correspondence. The M infrared ray-emitting tubes 16 and M infrared ray-receiving tubes 17 are all electrically connected with the circuit board 22. The M infrared ray-emitting tubes 16 are arranged at one side of the drip outlets 21 of the N drip hole passages 13; the M infrared ray-receiving tubes 17 are arranged at an opposite side of drip outlets 21 of the N drip hole passages 13; and the M infrared ray-emitting tubes 16 and the M infrared ray-receiving tubes 17 face each other.

Figure 5:
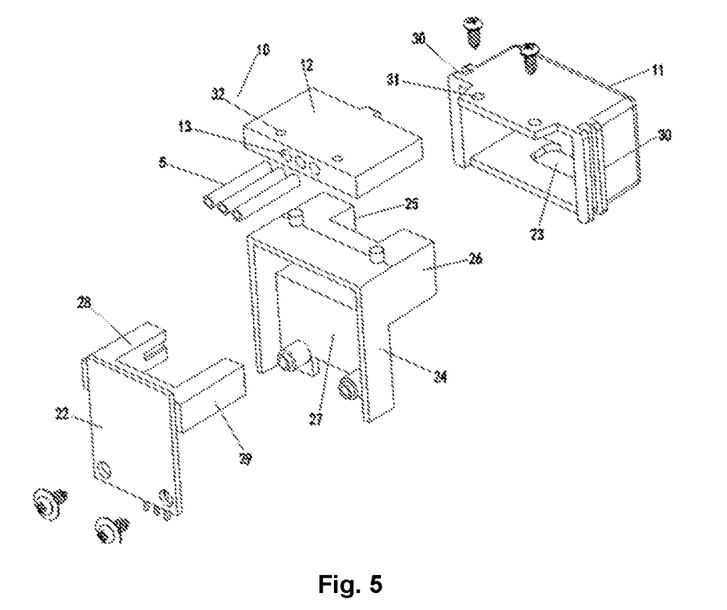
FIG. 5 is an exploded structural diagram of a drip number detection module in the present invention.

Further, as shown in FIG. 5, the drip number detection module 10 further includes a transparent inner cover 24 configured to contain the M infrared ray-emitting tubes 16, the M infrared ray-receiving tubes 17 and the circuit board 22 so as to separate the M infrared ray-emitting tubes 16, the M infrared ray-receiving tubes 17 and the circuit board 22 from the drip outlets 21 of the N drip hole passages 13. Specifically, a first transparent accommodating chamber 25, a second transparent accommodating chamber 26 and a waterproof protection cover 27 are integrally formed or machined on or connected with the inner cover 24. The first transparent accommodating chamber 25 and the second transparent accommodating chamber 26 are located at two sides of the drip outlets 21 of the N drip hole passages 13 respectively. The first accommodating chamber is configured to contain the M infrared ray-emitting tubes 16, the second accommodating chamber 17 is configured to contain the M infrared ray-receiving tubes 17, and the waterproof protection cover 27 is arranged between the N drip hole passages 13 and an outlet 23 so as to separate the outlet 23 from the circuit board 22. The M infrared ray-emitting tubes 16 and the M infrared ray-receiving tubes 17 are arranged on the discharging constraint cover 12 through the inner cover 24. Specifically, the circuit board 22 may be connected onto the discharging constraint cover 12 through the inner cover 24; or the M infrared ray-emitting tubes 16 and the M infrared ray-receiving tubes 17 are connected onto the discharging constraint cover 12 through the inner cover 24. Specifically, the M infrared ray-emitting tubes 16 may be emitting tubes with the model of IR928-6C and the M infrared ray-receiving tubes 17 may be receiving tubes with the model of PT333-3B.

Further, with continued reference to FIG. 5, a first mounting base 28, and a second mounting base 29 for mounting of the M infrared ray-receiving tubes are further fixedly connected onto the circuit board 22. The first mounting base 28 is arranged such that the M infrared ray-emitting tubes may be mounted on the first mounting base and the first mounting base may be inserted into the first transparent accommodating chamber 25. The second mounting base 29 is arranged such that the M infrared ray-receiving tubes may be mounted on the second mounting base and the second mounting base may be inserted into the second transparent accommodating chamber. Therefore, during assembly, firstly, the M infrared ray-emitting tubes 16 and the M infrared ray-receiving tubes 17 are correspondingly mounted on the first mounting base 28 and the second mounting base 29; and then the circuit board 22 is fixed to the inner cover 24. At this time, the first mounting base 28 is inserted into the first transparent accommodating chamber 25 and fixed, and the second mounting base 29 is inserted into the second transparent accommodating chamber 26 and fixed, and the circuit board 22 is fixed to the outer surface of the inner cover 24, thereby fixedly mounting the M infrared ray-emitting tubes 16, M infrared ray-receiving tubes 17 and the circuit board 22 (as shown in FIG. 6).

Preferably, as shown in FIG. 2 and FIGS. 4-6, the quantitative essential oil dripping device further includes an outer cover 11. The outer cover 11 is connected with the discharging constraint cover 12 and covers the outer side of the discharging constraint cover 12. Outlets 23 corresponding to the drip outlets 21 of the N drip hole passages 13 are integrally formed or machined in a bottom wall of the outer cover 11. The outlets 23 are located directly below the drip outlets 21 of the N drip hole passages 13 so as to allow the essential oil drips to drip from the drip outlets 21 of the N drip hole passages 13, thereby preventing the essential oil drips dripped from the drip outlets 21 of the N drip hole passages 13 from being affected by the external environment.

Figure 6:
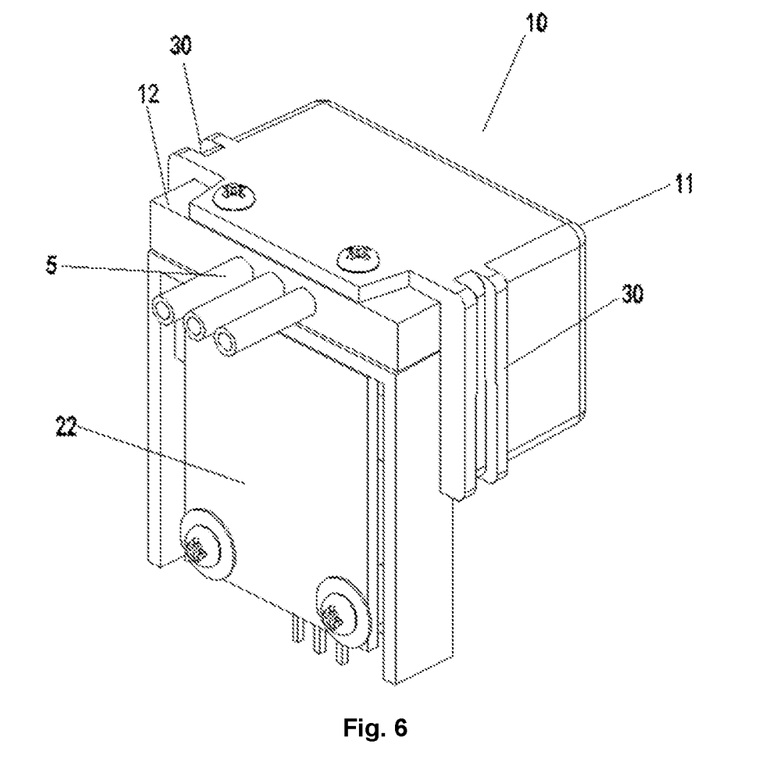
FIG. 6 is a combined structural diagram of a drip number detection module in the present invention.

Further, as shown in FIGS. 5 and 6, fixing grooves 30 for fixedly connecting the drip number detection module 10 with other structures or external structures of the quantitative essential oil dripping device are integrally formed or machined in or connected with an outer side wall of the outer cover 11. Preferably, the fixing grooves 30 are formed in two opposite sides of the outer cover 11 so as to ensure the stable mounting of the drip number detection module 10.

Specifically, a connection mode of the outer cover 11 with the discharging constraint cover 12 is as shown in FIG. 5. A fixing hole 31 is integrally formed or machined in the top wall of the outer cover 11, and a first threaded hole 32 is machined in a position, corresponding to the first fixing hole 31, of the top surface of the discharging constraint cover 12. When the discharging constraint cover 12 is fixed, a bolt may be used to connect with the first threaded hole 32 after passing through the first fixing hole 31 to fix the discharging constraint cover 12. Preferably, the inner cover 24 is arranged in the outer cover 11.

When there is no outer cover 11, the fixing groove 30 may be integrally formed or machined in or connected onto the discharging constraint cover 12 or the inner cover 24. The implementation mode and effects are the same as the implementation mode and effects when the fixing groove 30 is formed in the outer cover 11 and are not further described herein.

Specifically, as shown in FIG. 2 and FIG. 4, N is a positive integer greater than or equal to 2, and M=1. That is, the M group of infrared ray pair tubes 14 is one group of infrared ray pair tubes 14. The N drip hole passages 13 include N horizontal hole passages 19, and N vertical hole passages 20 correspondingly communicated with the N horizontal hole passages 19. A first end of each of the N horizontal hole passages 19 extends to an end surface of a first end of the discharging constraint cover 12, and the N horizontal hole passages 19 have the same length. Each two horizontal hole passages 19 in the N horizontal hole passages 19 are parallel to each other. Each two vertical hole passages 20 in the N vertical hole passages 20 are parallel to each other. This group of infrared ray pair tubes 14 is arranged at two sides directly below the N vertical hole passages 20 and configured to detect the essential oil drips dripped from the N vertical hole passages 20.

Figure 7:
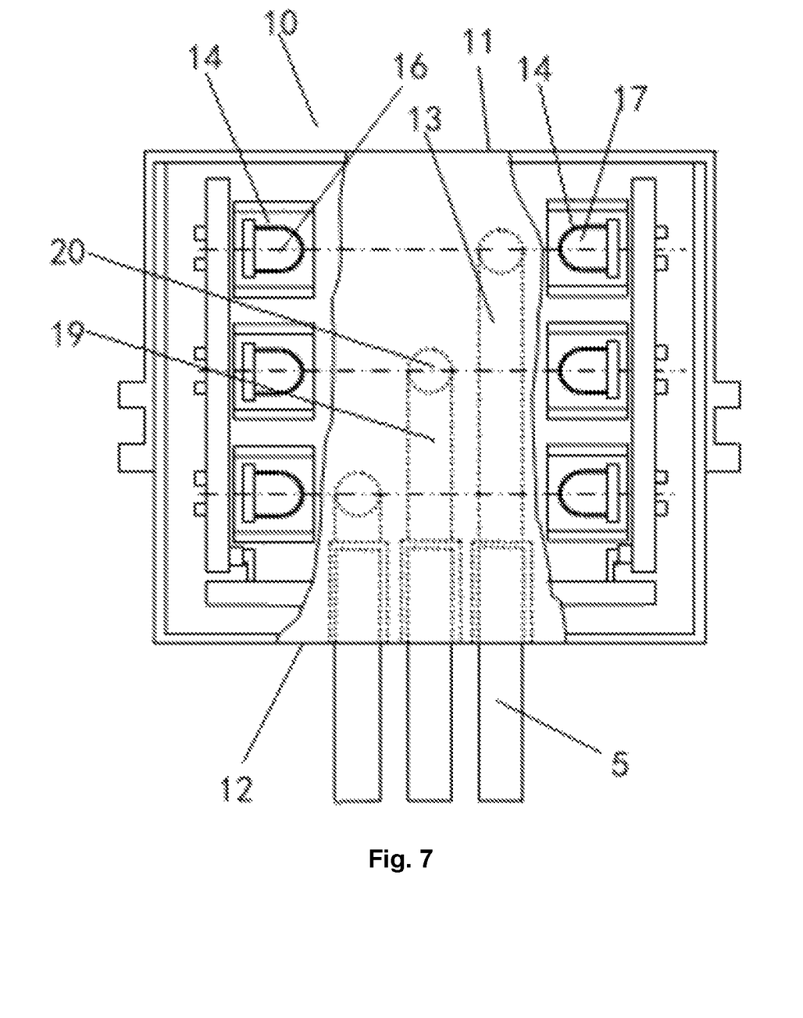
FIG. 7 is a structural diagram, viewed from above, of a second embodiment of a drip number detection module in the present invention.

Specifically, a second implementation mode of the drip number detection module 10 is as shown in FIG. 7. The drip number detection module 10 in this embodiment is merely different from the drip number detection module 10 in the first implementation mode in that: M=N and both M and N are positive integers greater than or equal to 2. The N drip hole passages 13 include N horizontal hole passages 19, and N vertical hole passages 20 correspondingly communicated with the N horizontal hole passages 19. A first end of each of the N horizontal hole passages 19 extends to an end surface of a first end of the discharging constraint cover 12, and the N horizontal hole passages 19 have different lengths. Each of the M groups of infrared ray pair tubes 14 corresponds to one vertical hole passage 20; each of the M groups of infrared ray pair tubes 14 is correspondingly arranged at two sides directly below the each of N vertical hole passages 20; and each of the M groups of infrared ray pair tubes 14 is configured to detect the essential oil drips dripped from one vertical hole passage 20.

Preferably, each two horizontal hole passages 19 in the N horizontal hole passages 19 are parallel to each other.

Specifically, a third implementation mode of the drip number detection module 10 is different from the drip number detection module 10 in the first implementation mode in that: M=1 and N=1, the N drip hole passage 13 is one drip hole passage 13; the M group of infrared ray pair tubes 14 is one group of infrared ray pair tubes 14; and the one group of infrared ray pair tubes 14 is arranged at two sides of the drip outlet 21 of the one drip hole passage 13. The one group of infrared ray pair tubes 14 only counts and detects the essential oil drips dripped from one drip hole passage 13.

The foregoing description is merely some embodiments of the present invention. Those of ordinary skill in the art may make some variations and improvements without departing from the creative concept of the present invention, and these variations and improvements all fall within the protection scope of the present invention.

We claim:

1. A quantitative essential oil dripping device (1), comprising:
   N sealed essential oil containers (40) configured to contain essential oil, wherein N is a positive integer greater than or equal to 1;
   N gas inlet tubes (4), of which gas outlets are inserted into the N essential oil containers (40) respectively; N oil outlet tubes (5), of which inlets are inserted into the N essential oil containers (40) respectively, wherein in each of the essential oil containers (40), the gas outlet of the gas inlet tube (4) is located above the inlet of the oil outlet tube (5);
   a gas pump (8) arranged at gas inlets of the N gas inlet tubes (4) and configured to fill the gas inlet tubes (4) with gas;
   a throttle valve (101) communicating the gas pump (8) with each of the essential oil containers (40) respectively; and
   a drip number detection module (10) configured to detect the drip number of the essential oil dripped from oil outlets of the N oil outlet tubes (5), the drip number detection module (10) comprises:
   a discharging constraint cover (12) with N drip hole passages (13) for insertion of and communication with the N oil outlet tubes (5);
   M groups of infrared ray pair tubes (14) which are arranged on the discharging constraint cover (12), correspond to drip outlets (21) of the N drip hole passages (13) in position, and are configured to detect essential oil drips, wherein M is a positive integer greater than or equal to 1; and
   a circuit board (22) electrically connected with the M groups of infrared ray pair tubes (14) and configured to perform counting.

2. The quantitative essential oil dripping device according to claim 1, further comprising:
   N passage-selection electromagnetic valves (6) arranged on the N gas inlet tubes (4) respectively and configured to control the opening or closing of the gas inlet tubes (4), so that the essential oil container (40) is communicated with or disconnected from the gas pump (8), and
   a main tube (7) communicated with the gas inlets of all the N gas inlet tubes (4), wherein
   the gas pump (8) is communicated with the gas inlets of the N gas inlet tubes (4) through the main tube (7); and
   the throttle valve (101) is arranged on the gas inlet tube (4) or the main tube (7) between the selection electromagnetic valve (6) and the gas pump (8).

3. The quantitative essential oil dripping device according to claim 2, further comprising: a pressure-relief electromagnetic valve (9) arranged on the main tube (7) and configured to communicate the main tube (7) with the outside or disconnect the main tube (7) from the outside.

4. The quantitative essential oil dripping device according to claim 3, wherein connection portions of the N gas inlet tubes (4) and the main tube (7) are all located between the gas pump (8) and the pressure-relief electromagnetic valve (9).

5. The quantitative essential oil dripping device according to claim 2, further comprising: a buffer gas-storage chamber (102) arranged at an end, away from the gas pump (8), of the main tube (7) and communicated with the main tube (7).

6. The quantitative essential oil dripping device according to claim 1, wherein the circuit board (22) comprises M groups of signal processing circuits which are electrically connected with the M groups of infrared ray pair tubes (14) and configured to convert an electrical signal generated by electrical connection of the M groups of infrared ray pair tubes (14) to a pulse signal; and
   a microprocessor electrically connected with the M groups of signal processing circuits and configured to perform counting according to the pulse signal.

7. The quantitative essential oil dripping device according to claim 1, wherein the M groups of infrared ray pair tubes (14) comprise M infrared ray-emitting tubes (16) and M infrared ray-receiving tubes (17) which are all arranged on the circuit board (22) and in one-to-one correspondence, wherein the M infrared ray-emitting tubes (16) are arranged at one side of drip outlets (21) of the N drip hole passages (13); the M infrared ray-receiving tubes (17) are arranged at an opposite side of drip outlets (21) of the N drip hole passages (13); and the M infrared ray-emitting tubes (16) and the M infrared ray-receiving tubes (17) face each other.

8. The quantitative essential oil dripping device according to claim 7, wherein the drip number detection module further comprises:
   a transparent inner cover (24) configured to contain the M infrared ray-emitting tubes (16), the M infrared ray-receiving tubes (17) and the circuit board (22) so as to separate the M infrared ray-emitting tubes (16), the M infrared ray-receiving tubes (17) and the circuit board (22) from the drip outlets (21) of the N drip hole passages (13), wherein
   the inner cover (24) is provided with a first transparent accommodating chamber (25) located at one side of the drip outlets (21) of the N drip hole passages (13) and configured to contain the M infrared ray-emitting tubes (16), and a second transparent accommodating chamber (26) located at the opposite side of the drip outlets (21) of the N drip hole passages (13) and configured to contain the M infrared ray-receiving tubes (17); and the M infrared ray-emitting tubes (16) and the M infrared ray-receiving tubes (17) are arranged on the discharging constraint cover (12) through the inner cover (24).

9. The quantitative essential oil dripping device according to claim 1, wherein N is a positive integer greater than or equal to 2, and M=1;

the N drip hole passages (13) comprise N horizontal hole passages (19), and N vertical hole passages (20) correspondingly communicated with the N horizontal hole passages (19);

a first end of each of the N horizontal hole passages (19) extends to an end surface of a first end of the discharging constraint cover (12), and the N horizontal hole passages (19) have the same length; and one group of infrared ray pair tubes (14) is arranged at two sides directly below the N vertical hole passages (20) so as to detect the essential oil drips dripped from the N vertical hole passages (20).

10. The quantitative essential oil dripping device according to claim 9, wherein each two horizontal hole passages (19) in the N horizontal hole passages (19) are parallel to each other; and each two vertical hole passages (20) in the N vertical hole passages (20) are parallel to each other.

11. The quantitative essential oil dripping device according to claim 1, wherein M=N and both M and N are positive integers greater than or equal to 2;

N drip hole passages (13) comprise N horizontal hole passages (19), and N vertical hole passages (20) correspondingly communicated with the N horizontal hole passages (19); a first end of each of the N horizontal hole passages (19) extends to an end surface of a first end of the discharging constraint cover (12), and the N horizontal hole passages (19) have different lengths; each of the M groups of infrared ray pair tubes (14) corresponds to one vertical hole passage (20); each of the M groups of infrared ray pair tubes (14) is correspondingly arranged at two sides directly below the each of N vertical hole passages (20); and each of the M groups of infrared ray pair tubes (14) is configured to detect the essential oil drips dripped from one vertical hole passage (20).

12. The quantitative essential oil dripping device according to claim 11, wherein each two horizontal hole passages (19) in the N horizontal hole passages (19) are parallel to each other.

13. The quantitative essential oil dripping device according to claim 1, wherein M=1 and N=1; the N drip hole passage (13) is one drip hole passage (13); the M group of infrared ray pair tubes (14) is one group of infrared ray pair tubes (14); and the one group of infrared ray pair tubes (14) is arranged at two sides of the drip outlet (21) of the one drip hole passage (13).

* * * * *